United States Patent [19]
Belin et al.

[11] Patent Number: 5,705,372
[45] Date of Patent: Jan. 6, 1998

[54] ENZYMATIC PROCESS FOR THE PREPARATION OF FLAVOURS, IN PARTICULAR THE IONONES AND $C_6$ TO $C_{10}$ ALDEHYDES

[75] Inventors: Jean-Marc Belin, Fontaine-Les-Dijon; Benoît Dumont, Gissey Sur Ouche; Françoise Ropert, Les Martres De Veyre, all of France

[73] Assignee: BFA Laboratories, Rocheville, France

[21] Appl. No.: 406,959

[22] PCT Filed: Sep. 27, 1993

[86] PCT No.: PCT/FR93/00943

§ 371 Date: Jun. 12, 1995

§ 102(e) Date: Jun. 12, 1995

[87] PCT Pub. No.: WO94/08028

PCT Pub. Date: Apr. 14, 1994

[30] Foreign Application Priority Data

Sep. 28, 1992 [FR] France ..................... 92 11513

[51] Int. Cl.⁶ ............... C12P 23/00; C12P 17/02; C12P 17/06; C12P 7/24
[52] U.S. Cl. ............... 435/123; 435/67; 435/125; 435/126; 435/147; 435/148
[58] Field of Search ............... 435/147, 148, 435/123, 125, 126, 67

[56] References Cited

U.S. PATENT DOCUMENTS

| | | | |
|---|---|---|---|
| 100,790 | 3/1870 | Gru et al. | 435/148 |
| 4,769,243 | 9/1988 | Kanisawa et al. | 426/33 |
| 5,464,761 | 11/1995 | Muller et al. | 435/147 |

FOREIGN PATENT DOCUMENTS 0481147  4/1992  European Pat. Off. .

OTHER PUBLICATIONS

Almosnino et al., "Apple pomace: an enzyme system for producing aroma compounds from polyunsaturated fatty acids", *Biotechnology Letters*, vol. 13, No. 12 (Dec. 1991).
Grosch et al., "Formation of volatile carbonyl compounds and cooxidation of beta-carotene by lipooxygenase from wheat, potato, flax and beans", *J. Agr. Food Chem.*, 24:456–459 (Jun. 1976).

*Primary Examiner*—Herbert J. Lilling
*Attorney, Agent, or Firm*—Merchant, Gould, Smith, Edell, Welter & Schmidt, P.A.

[57] ABSTRACT

The present invention relates to a novel enzymatic process for the preparation of flavors, in particular of the ionones and $C_6$ to $C_{10}$ aldehydes. The invention discloses a process for the preparation of optically active alpha ionone, beta ionone, $C_6$ aldehydes such as n-hexanal, trans-2-hexanal, $C_{10}$ aldehydes such as trans-2, cis-4-decadidienal, and trans-2, trans-4-decadienal. The invention also relates to a process for the production of alcohols, particularly $C_6$ and $C_{10}$ alcohols.

6 Claims, 1 Drawing Sheet

ENZYMATIC PROCESS FOR THE PREPARATION OF FLAVOURS, IN PARTICULAR THE IONONES AND $C_6$ TO $C_{10}$ ALDEHYDES

The present invention relates to a novel enzymatic process for the preparation of flavours, in particular of the ionones and $C_6$ to $C_{10}$ aldehydes. It relates more particularly to a process for the preparation of optically active alpha ionone, beta ionone, $C_6$ aldehydes such as n-hexanal, trans-2-hexenal, $C_{10}$ aldehydes such as trans-2, cis-4-decadienal and trans-2, trans-4-decadienal.

The production of flavouring additives presents complex problems since in most foodstuffs the natural flavour, which one attempts to reconstitute by means of flavourings, is the resultant of a mixture of many chemical compounds which it is most often difficult to define with precision.

It is known that two routes are open for the search for flavourings:

i) the production of synthetic molecules strictly identical with the natural molecules;

ii) the implementation of biotechnological processes such as micropropagation techniques, cell culture, microbial fermentations, enzymatic engineering.

It is this last procedure which is used in the present invention.

It is known that ionones, more particularly alpha-ionone and beta-ionone are found in many fruit flavours such as the raspberry, blackberry, blackcurrant, peach, apricot, melon, tomato, in the odour of plants such as the violet, *Boronia megastigma* in the flavour of transformed plants such as black tea, tobacco, carrot, vanilla or even in mushrooms such as the chanterelle.

Although they are present at very low concentrations, these substances play an important role in the flavour of these plants.

Moreover, the "green tones" which are due for example to n-hexanal having a green apple aroma or to trans-2-hexenal (odour of freshly cut grass) are extremely widespread among plants. Their contribution to the freshness tone of the products makes them flavouring substances of prime importance.

Other compounds, like the ionones, are derived from oxidative degradation of alpha- and beta-carotene by the same enzymatic pathways. Among others, the following compounds will be selected which can be obtained according to the process which is the object of the present invention:

dihydroactinidiolide, which is a lactone whose powerful odour recalls that of tea. This compound thus presents an interest for the flavouring industry;

5,6-epoxy-beta-ionone, which possesses a flavour similar to that of cedar wood, is more woody than that of beta-ionone. This substance thus also presents an interest for the flavouring industry.

Attempts to produce all of these compounds from natural sources in which they are usually present in minute quantities, which makes their extraction unattractive for economic reasons, have been abandoned.

Various studies including those of GROSCH et al. (J. Agric Food Chem. 24, 456–459, 1976) describe an enzymatic mechanism for the production of the ionones by means of lipoxygenases and unsaturated fatty adds, through co-oxidation of the carotenoids.

Furthermore, FISCHER and GROSCH (Z Lebenson, Unters.-Forsch, 165, 137–139, 1977) have obtained various aldehydes such as hexanal, 2,4-decadienal (two diastereoisomers), trans-2-hexenal and trans-2-octenal by placing together lipoxygenase $L_2$ of soya and linoleic acid.

Moreover, the American U.S. Pat. No. 4,769,243 describes a process for the preparation of green tones such as n-hexanal, 1-penten-3-ol, trans-2-hexenal and cis-2-pentenol (Ex. 1 and 2, column 5), by using a mixture constituted by ground soya seeds and unsaturated fatty adds in the presence of water (in the proportion of 3 to 20 times the weight of the soya seeds) and an addition of lipase. The reaction temperature is situated between 5° and 60° C. (preferably between 25° and 50° C.). The mixture is stirred for a period extending from 5 minutes to 24 hours (preferably 30 minutes to 10 hours) while a supply of air or oxygen is maintained throughout the reaction.

Finally, let us note that CHAN et al. (Biochim. Biophys. Acta, 398, 347–350, 1975) show that if oxygen is limiting, the formation of the long chain aldehydes such as 2,4-decadienal is favoured over that of the $C_6$ aldehydes.

These different enzymatic processes lead to the production of aldehydes and ionones but always in amounts difficult to make use of on an industrial scale.

The present inventors have developed a process making possible the production of flavours in high concentration.

According to the process of the present invention, a source or preparation of lipoxygenase and hydroperoxide-lyase, a natural source of unsaturated fatty acids and possibly a natural source of carotene are placed in contact for the purpose of biogenerating natural aldehydes and, optionally, the ionones.

According to the present invention, the enzymatic reaction occurs in a "pasty" mixture of high viscosity, which makes it possible to limit the transfer of the products to the medium and consequently to minimize the inhibitory effect that the product exerts on the reaction. In other words, the enzymatic oxidation of the invention occurs in a medium whose water content is relatively low, hence one in which bioreactants are concentrated. As a result, any factor which will increase the enzyme-substrates contact will accelerate the progress of the enzymatic reactions. Gas transfer is ensured by stirring the medium. Hence the enzymatic reactions are promoted by ensuring an intensified kneading of the various components. The yield of flavouring substances obtained according to the process of the invention is considerably higher than those obtained by the processes of the prior art.

The pasty medium of the process of the invention is a multi-phase reaction medium comprising in particular a solid phase, one or more liquid phases and one or more gaseous phases, the solid phase and the liquid phase(s) being present in proportions by weight of about 100:300 (solid:liquid). The solid phase may be constituted by a mixture of different solids, for example different flours, different plants or a mixture of flours and plants. The liquid phase(s) comprise(s) at least one oily phase. When there are several liquid phases, they are immiscible liquids.

More particularly, the invention consists of an enzymatic process for the preparation of flavours, in particular $C_6$ to $C_{10}$ aldehydes, by the placing of at least a source of lipoxygenase and hydroperoxide-lyase in contact with a source of polyunsaturated fatty adds, the reaction taking place with stirring in the presence of oxygen in a multi-phase medium comprising at least a solid phase and an oily phase characterized in that said medium contains per 100 parts of solid phase about 3 to 150 parts of an oily phase and possibly about 0 to 250 parts of an aqueous phase.

Typically, the medium is either a three-phase medium: solid phase, oily phase and gaseous phase, or a four-phase medium: solid phase, oily phase, aqueous phase and gaseous phase. These different phases are entirely or partially functional, i.e. they may be constituted of reagents implicated in the enzymatic reaction but may also comprise texturizing agents which contribute to the "pasty" texture of the medium The sources of lipoxygenase, hydroperoxide-lyase, polyunsaturated fatty adds and, optionally, carotene as well as texturizing agents are selected such that the reaction medium contains all of the phases mentioned above in suitable proportions for the production of the paste. For example, the source of lipoxygenase and hydroperoxide-lyase may constitute the solid phase or a part of this phase, and the source of polyunsaturated fatty adds may constitute the oily phase. The presence of the solid phase is essential for the production of a "pasty" medium. Within the different phases, the concentrations of the reagents are:

i) solid phase
  lipoxygenase activity: up to 1.5 mmole/min/g;
  carotene: 2.5 to 3 parts per thousand parts of solid phase (weight/weight), for example the solid part of carrot juice;
  polyunsaturated fatty adds: upto 2% linoleic add, upto 2% linolenic add.
ii) oily phase:
  polyunsaturated fatty acids: upto 78% linoleic add, upto 60% linolenic acid;
  carotene: upto 10% (oleoresin).

The percentages indicated above for the concentrations of reagents are weight/weight percentages of the phase in question.

The medium is advantageously a four-phase medium containing per 100 parts of solid phase, 3 to 120 parts of oily phase (for example 4 to 50) and 20 to 250 parts of aqueous phase (for example 50 to 200), the oily phase and the aqueous phase representing together less than 300 parts, and more particularly less than 250 parts. Typically, when the medium contains an aqueous source of carotene it contains per 100 parts of solid phase, 10 to 40 parts of oily phase and 80 to 200 parts of aqueous phase. When the medium does not contain an aqueous source of carotene it preferably contains per 100 parts of solid phase, 3 to 100 parts of oily phase and up to 100 parts of aqueous phase.

The aldehydes obtained according to this process are derived by oxidative degradation of the polyunsaturated fatty adds. The flavouring compounds differ according to the nature of the unsaturated fatty acids used.

The ionones obtained are alpha- and beta-ionones and epoxy-ionones and are produced as a result of the co-oxidation of the carotenoids by peroxide radicals released during the oxidation reaction of the unsaturated fatty acids.

It should be noted quite especially that the alpha-ionone obtained by the process is essentially the R(+) trans-alpha-ionone. Now this enantiomer preponderates to more than 90% in the natural flavours of the raspberry, violet, *Boronia megastigma*, black tea, carrot or even vanilla.

Finally we should note that it is possible to pass from the aldehyde (hexanal, hexenal) to the alcohol (hexanol, hexenol) by making use of bioprocesses implicating alcohol dehydrogenases.

According to a preferred embodiment of the invention the process comprises the plating of a source or preparation of lipoxygenase and hydroperoxidase-lyase, a natural source of polyunsaturated fatty adds and a natural source of carotene in contact, the reaction occurring in a mixer in a concentrated medium of high viscosity, oxygen being supplied to the reaction mixture by the input of air or oxygen or an air/oxygen mixture. The pressure which is maintained in the reaction medium is at least equal to the atmospheric pressure.

The different components of the bioreaction mixture may be obtained from the following sources:

Substances at various stages of purification derived from plants, animals or micro-organisms will be used as sources of lipoxygenases (E.C 1.13.11.12). The plant sources are particularly preferred, for example oleaginous plants such as soya, colza, sunflower; proteinaceous plants such as peas, beans, lupins; cereals such as wheat, maize, barley, oats, rice, rye, buckwheat, sorghum and triticale; tubers such as the potato and manioc. The cereals may be used in the form of whole grains, grain fractions (resulting for example from an enzymatic, chemical, thermal or mechanical treatment of the grain), or any other product derived from grinding of the grain such as flour or semolina, provided that their enzymatic activity is conserved. For example, the sources of lipoxygenases may be enzymatically active soya flour, germinated or ungerminated soya seeds. In the latter cases, the germinated or ungerminated soya seeds must preferably be ground with the aid of a grinder or a homogenizer without thermal inactivation of the enzymes present. The enzymatic activity of these preparations may be verified by employing the methods described by GROSCH et al. (supra).

Preferably soya flour, wheat flour or ground maize germs will be used as sources of lipoxygenase and hydroperoxidase-lyase. When the enzymes are used in this form, they constitute the solid phase.

The source of hydroperoxidase-lyase is usually the same as the source of lipoxygenases. This enzyme catalyses the cleavage of hydroperoxides formed during the oxidation reaction of the fatty acids, thus ensuring the production of the aldehydes.

The unsaturated fatty acids used in the process preferably have between 8 and 20 carbon atoms and are advantageously polyunsaturated.

Natural fatty acids such as oleic acid, linoleic acid, alpha-linolenic acid, eicosapentaenoic acid, arachidonic acid and ricinoleic acid will be used as source of fatty acids. It is also possible to use fats or oils of animal, plant or microbial origin containing these fatty acids, and which will be subjected to a preferably enzymatic lipolysis reaction by means of one or several lipases.

These fats or oils of plant origin may be for example the oils of soya, sunflower, saffron, olive, grape pip, maize germ, wheat germ, groundnut, sesame, nut, flax, cotton seed, borage, evening primrose, cynara as well as coconut butter oil.

These fats may also be of animal origin like butter, lard, codfish, sardine and various other fish and mammalian oils.

Hydrolysis will be effected by means of one or more lipases or by a preparation of lipases derived from micro-organisms, plants or animals. The lipase preparation may or may not be purified. Any lipase capable of carrying out the reaction on the fat or oil selected may be used. It may be a purified preparation containing a single enzyme or, alternatively, a mixture of several enzymes exhibiting a lipase activity. The enzyme possessing a lipase activity may be immobilized on a solid support. This reaction may be carried out prior to the lipoxygenase reaction or concomitantly. The amount of lipase added will usually vary from several tens to several hundreds of units per gram of oil or fat.

The source of polyunsaturated fatty acids, associated or not with lipases, may be added before during or after the grinding or mixing of the other starting materials, in a continuous or discontinuous manner.

When the medium contains a source of carotene, natural carotene will be used, derived from higher plants, algae or micro-organisms. It is alpha- and beta-carotene. The best sources are the carrot, palm oil and certain algae. The carotene may be in the form of oleoresin in which case it will form part of the oily phase. It may also be used in the form of an aqueous solution or even in the form of a suspension, for example concentrated carrot juice containing for example 20% suspended solids.

A suitable quantity or water or a solution containing the carotenoids or another aqueous phase, preferably corresponding to a value included between ⅓ and 2 times the mass of flour or soya seeds, is added. The aqueous phase may be added before, during or after grinding or mixing of the other starting materials in a discontinuous or continuous manner.

The medium may also contain texturizing agents for example glycerol as well as other additives such as emulsifying agents; agents making it possible to optimize enzymatic activity for example calcium chloride, ferrous sulfate and ascorbic acid. It is important to include the proportions of these additives in the calculation of the parts of each phase.

The reaction is conducted in a concentrated medium of high viscosity with stirring in the presence of air and/or oxygen under pressure.

Preferably, the oxygen is present in the form of a gas containing at least 21% oxygen, for example air, air enriched in oxygen or pure oxygen. This gas containing at least 21% oxygen constitutes the gaseous phase of the reaction mixture. Its incorporation into the medium is preferably such that the final apparent density, i.e. at the end of the reaction, is included between 0.9 and 0.4 $kg.L^{-1}$, for example 0.5 kg $L^{-1}$, and is a function of the following three parameters: the oxygen or air flow rate, the pressure under which the reaction is conducted and the stirring. The "apparent density" signifies the density of the medium comprising the incorporated gaseous phase.

The maximal flow rate of the air and/or oxygen injected during the bioreaction may attain 15 times the volume of the bioreaction mixture per minute, for example 2 or 4 times. If the flow rate is too high, high losses of flavours will occur as a result of entrainment. From 0 to 15 liters/min will be injected per liter of medium, for example from 1 to 2 l/min of air and/or oxygen per liter of pasty mixture.

The pressure of air and/or oxygen within the reactor (mixer-malaxator) is included between atmospheric pressure and 50 bars (about $50 \times 10^5$ Pa), for example between 8 bars (about $8 \times 10^5$ Pa) and 25 bars (about $25 \times 10^5$ Pa).

Depending on the quantity of oxygen derived from air and/or pure oxygen injected into the reactor and the intensity of the pressure in the reactor, the reaction will terminate with the formation of "short chain" aldehydes (such as n-hexanal, trans-2-hexenal, etc. . . . ) or "long chain" aldehydes (such as 2,4-decadienal, etc. . . . ).

Stirring of the medium is carried out by any appropriate means, preferably by a stirrer of the planetary gear type used at a speed of rotation included between 20 and 200 rev./min., for example 60 to 150 rev./min.

During the bioreaction the temperature will usually be maintained between 10° and 60° C., and preferably between 20° and 40° C.

As regards the viscosity of the pasty medium, it may be characterized with the aid of two types of measurements, namely:

a) the force of compresssion, the value of which was included during the tests performed between 3N (for a mixture with 55% water) and 5N (for a mixture with 45% water);

b) the force of adhesion, the value of which was included during the tests performed between 5N and 8N.

The duration of the reaction will usually be included between 5 and 48 hours, and preferably between 10 and 24 hours.

The reaction is usually carried out at a pH included between 4.5 and 10, more usually between 5 and 7.

The volatile fraction containing the flavours will be extracted by any appropriate means such as accelerated hydro-distillation, for example in a turboextractor or by steam distillation or also by means of supercritical $CO_2$.

A final purification step will be carried out in which use will be made in particular of fractional distillation with cyclodextrins.

The yields of ionones and aldehydes according to the invention can be exploited on an industrial scale For example, the concentration of alpha- and beta-ionones may attain between 100 and 400 mg/kg medium The concentration of aldehydes may attain 1000 mg/kg medium.

The process of the invention is preferably applied to the production of optically active alpha-ionones, beta-ionones, n-hexanal, trans-2-hexenal, trans-2, cis-4-decadienal, trans-2, trans-4-decadienal, 5,6-epoxy-beta-ionone and dihydroactinidiolide.

The invention also relates to an enzymatic process for the production of alcohols, in particular $C_6$ to $C_{10}$ alcohols, characterized in that it comprises:

i) the preparation of $C_6$ to $C_{10}$ aldehydes according to the process of the invention described above;

ii) the placing of the aldehydes obtained in i) in contact with one or more alcohol dehydrogenases;

iii) the recovery of the alcohols thus obtained.

According to this variant of the invention one or more alcohol dehydrogenase(s) is/are used. This step of the process may be performed concomitantly with or subsequent to the oxidation reaction. The production of cis-3-hexenol and hexanol is particularly preferred.

The above characteristics as well as other characteristics and minor advantages will become more completely apparent in the detailed description of embodiments given as a non-limiting guide in the examples below by using the equipment which is shown in the only appended FIGURE.

BRIEF DESCRIPTION OF DRAWING

In this FIGURE a reactor is shown schematically within which are advantageously carried out the operations of homogenization, malaxation and oxygenation of the viscous mixture as well as the bioreaction which gives rise to the formation of the flavours by means of enzymatic oxidation.

This reactor is composed of a leak-tight chamber or tank 1, the upper part of which is closed by a fixed cover 2 in which a moving plate 2a can rotate supported by a main rotating axis 3. Rotating joints 4 make possible the rotation of said plate 2a, while leaving the chamber 1 stationary and ensuring leak-tightness.

Figure 1:
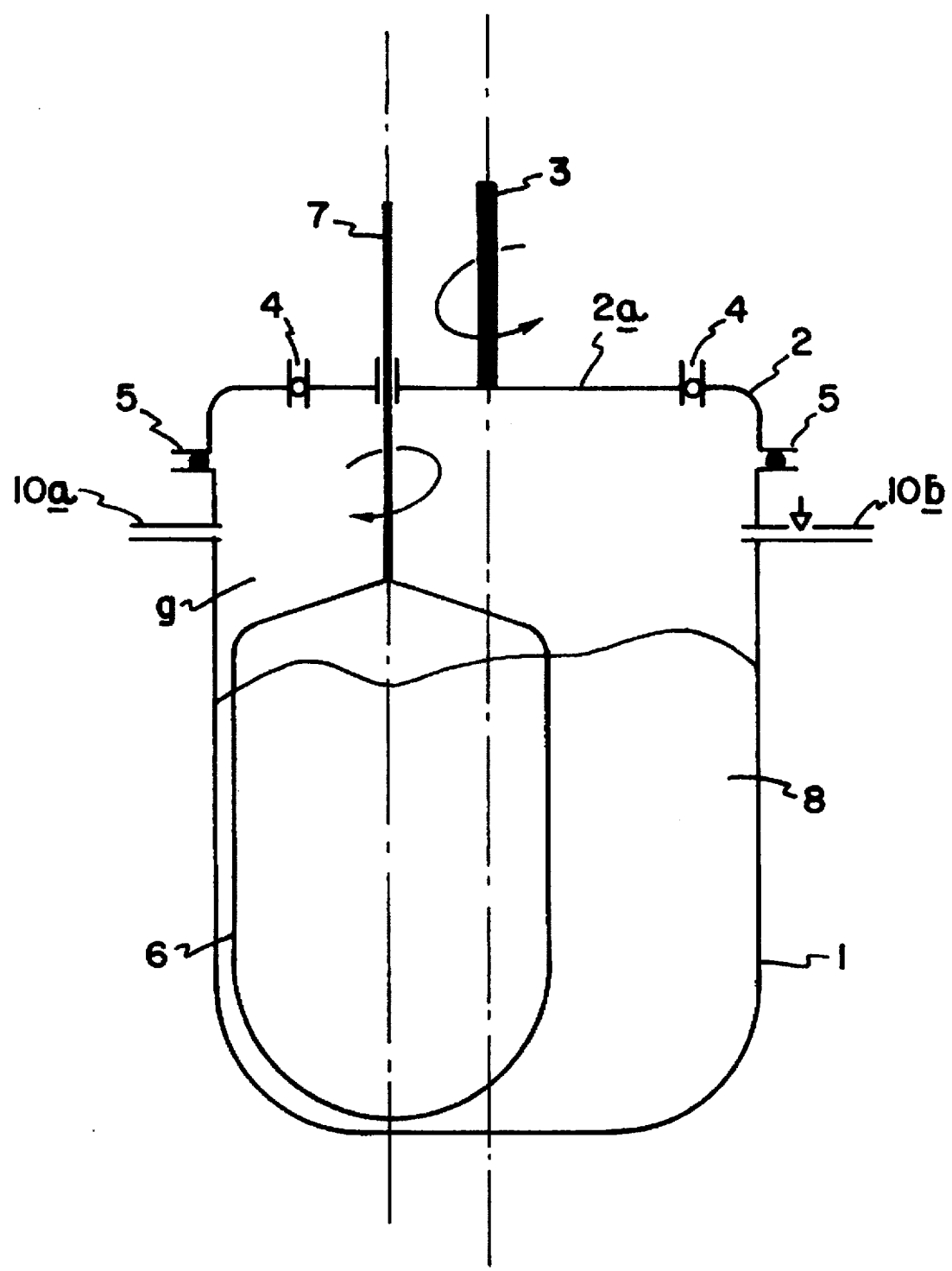

The fixed cover 2 is fitted tightly to the chamber 1 through the intermediary of a circular fixed joint 5. A rotating tool 6, responsible for the mixing and malaxing functions by planetary gear movement, is made to rotate by a secondary rotating axis 7. This rotating tool 6 which constitutes the mechanical stirring device of the viscous medium 8, simultaneously is responsible for its homogenization and oxygenation within the leak-tight chamber 1. This rotating tool may be either a loop, or a blade or a paddle or any framework made of metal or other chemically inert substance.

A free atmosphere 9 above the viscous medium composed of air, an air/oxygen mixture or pure oxygen under a pressure of the order of 1 to 8 bars is in contact with the viscous medium 8 kneaded by the rotating tool 6. The gaseous medium is injected into the chamber of the reactor through the flow pipe 10a whereas provision is made for the permanent escape of the same gaseous mixture through the intermediary of a pipe 10b which provides a controlled escape so as to ensure the permanent renewal of the gaseous fluid at a rate of two times the volume of fluid per minute, while maintaining the pressure in the chamber at the desired value for the bioreaction.

The combined effects of the pressure and the atmosphere renewal have the result of optimizing the oxygenation conditions of the viscous medium.

The examples below which make use of the reactor described above illustrate several compositions characteristic of mixtures making use of the process of the present invention for the purpose of the enzymatic production of ionones and $C_6$–$C_{10}$ aldehydes. In all of the examples the compositions are defined as weight percentages calculated on the basis of the total mass of the various components.

EXAMPLES

Example 1

The bioreaction mixture was prepared in a mixer-malaxer of the reactor type previously described of 6 liters internal volume, with stirring.

This mixture is constituted of soya flour (full-fat raw enzymatic) in the proportion of 35.25%, carrot oleoresin in the proportion of 4.41%, saffron oil in the proportion of 9.30% and water in the proportion of 48.96%.

These proportions correspond to 100 parts of solid phase, 38.9 parts of oily phase and 138.9 parts of aqueous phase.

In this way an emulsion of the components is produced in the aqueous phase. The hydrolysis of the saffron oil proceeds simultaneously with the generation of the flavouring substances as a result of the addition of 828 KU of lipase. The enzymatic activities involved require the addition of calcium chloride (in the proportion of 1.18%), ferrous sulfate (in the proportion of 0.09%) and ascorbic acid (in the proportion of about 0.01%).

A viscous medium was obtained which was malaxated at 90 rev./min at 25° C. The supply of oxygen to the mixture was ensured by a continuous delivery of pure oxygen at a rate of 0.5 L/min under atmospheric pressure.

The apparent density of the medium is included between 0.7 and 0.8 kg/l.

The flavouring substances synthesized were extracted by steam distillation under atmospheric pressure for different times of bioproduction. The volatile fraction is analyzed by gas phase chromatography and optionally by mass spectrometry.

The best concentrations of ionones obtained after a reaction time of 26 hours are 95 mg/kg of paste for alpha-ionone and 300 mg/kg of paste for beta-ionone. The concentration of 5,6-epoxy-beta-ionone is 575 mg/kg of paste and the concentration of dihydroactinidiolide is 130 mg/kg of paste.

The alpha-ionone produced is optically active. The enantiomer obtained is very predominantly the R(+) trans-alpha-ionone.

Example 2

The protocol described in Example 1 was repeated, with the difference that the flow rate of oxygen supplied to the reaction mixture is doubled (1 L/min).

The duration of the bioreaction was still 26 hours and it was observed that the concentrations of ionones and dihydroactinidiolide were similar to those obtained in Example 1.

It was observed that the maximal concentrations of the four compounds taken into consideration were more rapidly attained.

Example 3

The protocol described in Example 1 was repeated, with the difference that the supply of oxygen to the bioreaction mixture is ensured by a continuous flow of air at a rate of 1.5 L/min.

The duration of the bioreaction was still 26 hours and it was observed that the concentrations of 5,6-epoxy-beta-ionone and dihydroactinidiolide increased throughout the time of reaction and attained the values of 1000 mg/kg of paste and 300 mg/kg of paste, respectively, at the 26th hour.

As for the concentrations of beta- and alpha-ionones, they reached their maximal values at the 20th hour and remained stable upto the end of the bioreaction. At the 26th hour, the concentrations of beta- and alpha-ionones were 230 mg/kg of paste and 100 mg/kg of paste, respectively.

Example 4

The bioreaction mixture was prepared in a mixer-malaxer of the reactor type previously described of 6 liters internal volume, with stirring.

In this example, the mixture is constituted of carrot juice (20% suspended solids) in the proportion of 65.87%, soya flour in the proportion of 25.80% and saffron oil in the proportion of 6.81%.

These proportions correspond to 100 parts of solid phase, 17.47 parts of oily phase and 134.9 parts of aqueous phase.

An addition of 595 KU of lipase was made as were additions of calcium chloride (in a proportion of 0.86%), ferrous sulfate (in a proportion of 0.07%) and ascorbic acid (in a proportion of about 0.01%).

A viscous medium was obtained which was treated under the same conditions as in Example 2 (continuous flow of pure oxygen at a rate of 1 L/min under atmospheric pressure).

After a bioreaction time of 12 hours, the concentrations of beta- and alpha- ionones reached the values of 210 mg/kg of paste and 185 mg/kg of paste, respectively.

As regards the concentrations of 5,6-epoxy-beta-ionone and dihydroactinidiolide, they reached the values of 140 mg/kg of paste and 20 mg/kg of paste, respectively, after a reaction time of 12 hours.

At the 24th hour, they were 510 mg/kg of paste and 50 mg/kg of paste, respectively.

In addition, appreciable concentrations of n-hexanal and 2,4-decadienal (trans-2, trans-4-decadienal and trans-2, cis-4-decadienal forms) which attained the values of 950 mg/kg and 1020 mg/kg of paste, respectively, were obtained at the 24th hour.

Example 5

The protocol described in Example 4 was repeated, with the difference that the additions of iron sulfate and ascorbic acid were omitted.

The bioreaction was allowed to proceed for 28 hours and it was observed that the concentrations of beta- and alpha-ionones reached the values of 255 mg/kg of paste and 180 mg/kg of paste, respectively, after a reaction time of 16 hours.

As regards the concentrations of 5,6-epoxy-beta-ionone and dihydroactinidiolide, they reached the values of 80 mg/kg of paste and 85 mg/kg of paste respectively, after a bioreaction time of 16 hours.

In addition, at the 16th hour, concentrations of n-hexanal and 2,4-decadienal of 155 mg/kg of paste and 200 mg/kg of paste, respectively, were obtained. Measurements made after a bioreaction time of 21 hours gave values of 220 mg/kg of paste and 210 mg/kg of paste, respectively.

Example 6

The protocol described in Example 5 was repeated with the difference that the flow rate of oxygen passed through the bioreaction mixture was doubled (2 L/min. under atmospheric pressure).

The bioreaction time was still 28 hours and it was observed that the concentrations of beta- and alpha-ionone reached the values of 180 mg/kg of paste and 130 mg/kg of paste respectively, after a bioreaction time of 16 hours. Measurements made after a bioreaction time of 28 hours gave the values of 270 mg/kg of paste and 175 mg/kg of paste, respectively, i.e. values of the order of 50% higher.

As regards the concentration of 5,6-epoxy-beta-ionone, it was 130 mg/kg of paste at the 16th hour and reached the value of 255 mg/kg of paste at the 28th hour. The concentration of dihydroactinidiolide had then attained the value of 100 mg/kg of paste.

As regards the concentrations of n-hexanal and 2,4-decadienal they reached the values of 920 mg/kg of paste and 280 mg/kg of paste, respectively, after a bioreaction time of 21 hours.

Example 7

The bioreaction mixture was prepared in a mixer-malaxer of the reactor type previously described of 6 liters internal volume, with stirring.

In this example, the mixture is constituted of concentrated carrot juice (20% suspended solids) in the proportion of 77.67%, soya flour in the proportion of 16.05% and saffron oil in the proportion of 5.18%.

These proportions correspond to 100 parts of said phase, 16.40 parts of oily phase and 196.36 parts of aqueous phase.

An addition of 450 KU of lipase was made as was an addition of calcium chloride (in the proportion of 0.65%).

It will be noticed that in this example, as compared to Examples 4, 5 and 6, the concentration of carrot juice was increased and that, reciprocally, the concentrations of soya flour, saffron oil and lipase were diminished.

The bioreaction mixture obtained was treated under the same conditions as in Example 2 (oxygen flow rate: 1 L/min., at atmospheric pressure).

The bioreaction was carried out for 35 hours and it was observed that the concentrations of beta- and alpha-ionones were only 78 mg/kg of paste and 70 mg/kg of paste, respectively, at the 35th hour. In addition, they had progressed only very slowly during the reaction up to the 35th hour.

As regards the concentration of 5,6-epoxy-beta-ionone, it was 70 mg/kg of paste after a bioreaction time of 35 hours. At the same time, the concentration of dihydroactinidiolide attained the value of 80 mg/kg of paste.

As regards the concentrations of n-hexanal and 2,4-decadienal, they reached the values of 250 mg/kg of paste and 75 mg/kg of paste after a bioreaction time of 35 hours.

Example 8

The bioreaction mixture was prepared in a mixer-malaxer of the reactor type previously described of 80 liters internal volume, with stirring.

This mixture is constituted by concentrated carrot juice (20% suspended solids) in the proportion of 55.50%, soya flour in the proportion of 37.50% and saffron oil in the proportion of 5.72%.

These proportions correspond to 100 parts of solid phase, 11.76 parts of oily phase and 91.02 parts of aqueous phase.

An addition of 16 500 KU of lipase was made as was an addition of calcium chloride (in the proportion of 0.72%).

A viscous paste was obtained which was malaxated at 70 rev./min at 26°+/−1° C. The oxygen supply to the mixture was ensured by a continuous flow of air at a rate of about 10 L/min. The atmosphere above the bioreaction mixture was under a pressure of 2 bars.

The bioreaction was carried out for 40 hours and it was observed that the concentration of alpha-ionone produced was 230 mg/kg of paste at the 40th hour whereas it was only 110 mg/kg of paste after a bioreaction time of 24 hours.

It was observed that beta-ionone was only present in trace amounts.

As regards the concentration of 5,6-beta-ionone it remained low throughout the bioreaction and reached the value of only 23 mg/kg of paste at the 30th hour.

As regards the concentration of n-hexanal, this latter continued to increase throughout the bioreaction to reach 802 mg/kg of paste at the 24th hour and 980 mg/kg of paste at the 40th hour.

The same was true for 2,4-decadienal and in even more marked proportions since its concentration, which reached 116 mg/kg of paste at the 24th hour, increased to 232 mg/kg of paste at the 40th hour, i.e. it doubled its value.

Example 9

The bioreaction mixture was prepared in a mixer-malaxer of the reactor type previously described of 6 liters internal volume, with stirring.

This mixture is constituted of soya flour in the proportion of 47.30%, saffron oil in the proportion of 1.97% and water in the proportion of 49.27%. An emulsion of the components was thus produced in the aqueous phase.

These proportions correspond to 100 parts of solid phase, 4.16 parts of oily phase and 103.9 parts of aqueous phase.

An addition of 347 KU of lipase was made as was an addition of calcium chloride (in the proportion of 0.80%), ferrous sulfate (in the proportion of 0.07%) and ascorbic acid (in the proportion of about 0.01%).

A viscous medium was obtained which was malaxated at 110 rev./min at 26°+/−1° C. The oxygen supply to the mixture was ensured by a continuous flow of air at a rate of 1.66 L/min., at atmospheric pressure.

The flavouring substances synthesized were extracted by steam distillation at atmospheric pressure for different bioreaction times.

The bioreaction was carried out for 23 hours and it was observed that the concentrations of n-hexanal and 2,4-decadienal, the principal flavouring compounds obtained in the present experiment, attained the values of 1.71 g/kg of paste and 0.70 g/kg of paste, respectively, after a bioreaction time of 23 hours.

The analysis of the volatile fraction by gas phase chromatography revealed in addition the presence of trans-2-hexenal, trans-2-nonenal and 2,6-nonadienal, in particular.

Example 10

The protocol described in Example 9 was repeated with the difference that the quantity of saffron oil was increased to the detriment of the concentration of soya flour (45.33%) (100 parts of solid phase, 8.76 parts of oily phase and 108.4 parts of aqueous phase).

A viscous medium was obtained which was malaxated at 100 rev./min at 25°+/−1° C. The bioreaction was carried out for 23 hours and it was observed that the concentrations of n-hexanal and 2,4-decadienal reached the values of 3.40 g/kg of paste and 0.86 g/kg of paste, respectively, at the 23rd hour.

Example 11

The bioreaction mixture was prepared in a mixer-malaxer of the reactor type previously described of 80 liters internal volume, with stirring.

This mixer is constituted by soya flour in the proportion of 50.23%, saffron oil in the proportion of 3.59% and water in the proportion of 44.85%. An emulsion of the components was thus produced in the aqueous phase.

These proportions correspond to 100 parts of solid phase, 6.96 parts of oily phase and 89.25 parts of aqueous phase.

An addition of 14 600 KU of lipase was made as was an addition of calcium chloride (in the proportion of 0.73%), ferrous sulfate (in the proportion of 0.07%) and ascorbic acid (in the proportion of about 0.01%).

A viscous paste was obtained which was malaxated at 70 rev./min. at 32°+/−1° C. The oxygen supply to the mixture was ensured by a continuous flow of air at a rate of about 10 L/min. The atmosphere above the bioreaction mixture was under a pressure of 2 bars.

The bioreaction was carried out for 17 hours. It was observed that the two principal flavouring substances present in the volatile fraction were n-hexanal and 2,4-decadienal. They reached concentrations of 2.99 g/kg of paste and 0.40 g/kg of paste, respectively, after a bioreaction time of 17 hours.

Although the present process has been described with reference to specific examples of the embodiment, it is quite evident to any specialist skilled in the art that it is possible to introduce a variety of detailed modifications without exceeding the limits of the framework of the invention.

We claim:

1. An enzymatic process for preparing flavors, said process comprising the steps of:

(a) placing at least a source of lipoxygenase and hydroperoxide in contact with a source of unsaturated fatty acids to form a first medium;

(b) reacting said first medium in the presence of oxygen while stirring in a multiphase medium to produce a flavor, said multiphase medium comprising at least a solid phase and an oily phase, wherein said multiphase medium contains per 100 parts of solid phase, about 3 to 150 parts of oily phase, and about 0 to 250 parts of an aqueous phase, wherein said oxygen is in a gaseous phase containing at least 21% oxygen and said gaseous phase is selected from the group consisting of air, oxygen-enriched air, and pure oxygen and wherein said gaseous phase is incorporated into said reaction medium such that the final apparent density of the medium is between about 0.9 and 0.4 kg/l; and (c) recovering said flavors produced in said multiphase medium.

2. The process according to claim 1, wherein said reacting step (b) is conducted under a pressure between atmospheric pressure and 50 bars, and the oxygen flow rate is between 0 and 15 liters per kg of medium.

3. The process according to claim 1, wherein said reaction medium further comprises a source of carotene.

4. The process according to claim 1, wherein the multiphase medium comprises per 100 parts of solid phase, 3 to 120 parts of an oily phase and 20 to 250 parts of an aqueous phase, said oily phase and aqueous phase being less than 300 parts.

5. The process according to claim 1, wherein said flavors which are prepared are selected from the group of optically active alpha-ionone, beta-ionone, n-hexanal, trans-2-hexenal, trans-2, cis-4-decadienal, trans-2, trans-4 decadienal, 5,6-epoxy-beta-ionone and dihydroactinidiolide.

6. The process according to claim 1, wherein said stirring of said reacting step (b) is carried out by a planetary gear stirrer having a speed of rotation between 20 and 200 rev./min.

* * * * *